US 9,770,038 B2

(12) United States Patent
Liu et al.

(10) Patent No.: US 9,770,038 B2
(45) Date of Patent: Sep. 26, 2017

(54) HUMAN-DERIVED INSECT-RESISTANT GENE AND ANTI-CRY1B TOXIN IDIOTYPE SINGLE-CHAIN ANTIBODY ENCODED THEREBY AND APPLICATION THEREOF

(71) Applicant: JIANGSU ACADEMY OF AGRICULTURAL SCIENCES, Xuanwu Nanjing (CN)

(72) Inventors: Xianjin Liu, Xuanwu Nanjing (CN); Chongxin Xu, Xuanwu Nanjing (CN); Xiao Zhang, Xuanwu Nanjing (CN); Yuan Liu, Xuanwu Nanjing (CN); Yajing Xie, Xuanwu Nanjing (CN); Cunzheng Zhang, Xuanwu Nanjing (CN); Xiangyang Yu, Xuanwu Nanjing (CN); Donglan Wang, Xuanwu Nanjing (CN)

(73) Assignee: JIANGSU ACADEMY OF AGRICULTURAL SCIENCES INSTITUTE OF FOOD SAFETY AND MONITORING TECHNOLOGY, Xuanwu Nanjing (CN)

( * ) Notice: Subject to any disclaimer, the term of this patent is extended or adjusted under 35 U.S.C. 154(b) by 0 days.

(21) Appl. No.: 15/104,127

(22) PCT Filed: Jan. 9, 2015

(86) PCT No.: PCT/CN2015/070421
§ 371 (c)(1),
(2) Date: Jun. 13, 2016

(87) PCT Pub. No.: WO2015/109952
PCT Pub. Date: Jul. 30, 2015

(65) Prior Publication Data
US 2017/0035055 A1   Feb. 9, 2017

(30) Foreign Application Priority Data
Jan. 26, 2014 (CN) .......................... 2014 1 0037175

(51) Int. Cl.
*A01N 63/02* (2006.01)
*C07K 16/12* (2006.01)
*C12N 15/70* (2006.01)

(52) U.S. Cl.
CPC .............. *A01N 63/02* (2013.01); *C07K 16/12* (2013.01); *C07K 16/1278* (2013.01); *C12N 15/70* (2013.01); *C07K 2317/622* (2013.01)

(58) Field of Classification Search
None
See application file for complete search history.

(56) References Cited

FOREIGN PATENT DOCUMENTS

| CN | 103773774 A | 5/2014 |
|---|---|---|
| CN | 103773775 A | 5/2014 |
| CN | 103773776 A | 5/2014 |

OTHER PUBLICATIONS

Zhang et al. "Rapid isolation of single-chain antibodies from a human synthetic phage display library for detection of Bacillus thuringiensis (Bt) Cry1B toxin" Ecotoxicology and Environmental Safety, May 23, 2012, ISSSN 0147-6513, pp. 84-90.

Kabir et al. "An improved phage-display panning method to produce an HM-1 killer toxin anti-idiotypic antibody" BMC Biotechnology, vol. 9, Dec. 14, 2009, ISSN 1472-6750, Document No. 99.

Oddou et al. "Immunologically unrelated *Heliothis* sp. and *Spodoptera* sp. midgut membrane-proteins bind Bacillus thuringiensis CrylA(b) S-endotoxin" Eur. J. Biochem., vol. 212, No. 1, Feb. 15, 1993, ISSN 0014-2956, pp. 145-150.

Huang et al. "Advances in Research on Anti-idiotypic Antibody" Guangxi Journal of Light Industry, No. 4, Apr. 30, 2009, ISSN 1003-2673, pp. 9-11.

International Search Report for International Application No. PCT/CN2015/070421, dated Mar. 30, 2015.

*Primary Examiner* — Robert A Zeman
(74) *Attorney, Agent, or Firm* — Heslin Rothenberg Farley & Mesiti P.C.

(57) ABSTRACT

Provided are a human-derived insect-resistant gene having a nucleotide sequence represented by SEQ ID NO.1, and an anti-Cry1B toxin idiotype single-chain antibody encoded by said human-derived insect-resistant gene and having an amino acid sequence represented by SEQ ID NO.2. The idiotype single-chain antibody is a β-type and has insecticidal activity, and after expression by the prokaryotic system, the primary culture thereof has binding activity to *Cnaphalocrocis medinalis* midgut peritrophic membrane specific receptor BBMV.

2 Claims, 2 Drawing Sheets

US 9,770,038 B2

HUMAN-DERIVED INSECT-RESISTANT GENE AND ANTI-CRY1B TOXIN IDIOTYPE SINGLE-CHAIN ANTIBODY ENCODED THEREBY AND APPLICATION THEREOF

CROSS REFERENCE TO RELATED APPLICATIONS

This application is a national stage filing under section 371 of International Application No. PCT/CN2015/070421, filed on Jan. 9, 2015, and published in Chinese on Jul. 30, 2015, as WO 2015/109952 A1 and claims priority of Chinese application no. 201410037175.X filed on Jan. 26, 2014, the entire disclosure of these applications being hereby incorporated herein by reference.

SEQUENCE LISTING

This application contains a Sequence Listing in Computer Readable Form; the file, in ASCII format, is designated H0712937.txt, which is 4.1 kilobytes in size and was created on Oct. 5, 2015. The sequence listing file is hereby incorporated by reference in its entirety into the application.

FIELD OF THE INVENTION

The present invention relates to genetic engineering and biological control field, particularly to a human-derived insect-resistant gene and anti-Cry1B toxin idiotype single-chain antibody thereby and application thereof.

BACKGROUND OF THE INVENTION

Currently, the insecticidal gene widely used in the world for biological control of pests is Bt toxin gene of *Bacillus thuringiensis* (Bt) (such as: Cry1B, Cry1Ab, Cry1Ac, Cry1C and Cry1F et al.). *Bacillus thuringiensis* is insect pathogenic bacterium. The Bt toxin generated by it has a specific killing effect to many species of agricultural and forestry pests. Since Belgian Plant Genetic Systems first reported the success of transgenic Bt insect-resistant tobacco in 1987 till today, Bt gene has been transferred to main crops in the world, such as: maize, paddy, cotton, tomato, potato and tobacco. According to the statistics of International Service for the Acquisition of Agri-biotech Applications (ISAAA) in 2012, the area of transgenic Bt cotton grown in China has exceeded 3.9 million hectares, accounting for 71.5% of the total area of the cotton grown in China. However, following the application and generalization of transgenic Bt crops, its possible potential hazards in gene escape, change of microbial ecological structure of soil, drug resistance of species and harm to normal immune system have gradually aroused the attention of the society. "Diversity of Rhizospheric Microorganisms and Bacterial Physiological Groups of Transgenic Bt Maize" (Wang Min et al., Chinese Journal of Ecology, Issue 03 of 2010) and "Influence of Transgenic Bt Maize on Bacterial Quantity and Diversity of Soil" (Liu Ling et al., Journal of Ecology and Rural Environment, Issue 03 of 2011) analyzed the bacterial quantity and diversity of the soil in which transgenic Bt maize is grown indoors and outdoors. The results all show significant difference between the transgenic Bt maize growing group and the blank control group.

"Cry1Ac protoxin from *Bacillus thuringiensis* sp. kurstaki HD73 binds to surface proteins in the mouse small intestine" (Vázquez-Padrón et al., Biochem Biophys Res Commun, Issue 01, 2000) discovered that when intrinsic toxic protein of Bt and extrinsic toxic protein of Bt taken in by a mouse reached 10 mg/kg and 100 mg/kg, T cell ANAE positive rate, spleen index and macrophage phagocytosis of the mouse all were inhibited obviously during animal experiment. The more the intake is, the more obvious the inhibiting effect will be. This experiment also discovered that when the cumulative coefficient of Bt toxin protein in animal body was greater than 6.24, it might result in injury of liver, kidney and gastrointestinal tract and in liver and kidney, anomalies of cellular swelling and vacuolar degeneration could be observed and glomerular vascular epithelial lesion could be seen. Of course, it can't be excluded that they were caused by immunoreactions. Meanwhile, long-term use of Bt toxin protein at a large dose may also result in significant decrease of total white blood cells (WBC) and hemoglobin (HGB) of animals. This also indicates Bt toxin protein has obvious toxicity of immunosuppression. Therefore, developing substitute biological effectors with Bt toxin bioactivity (such as: anti-idiotype antibody) is a research hotspot in biological pest development field.

As humanized antibody gene is derived from human, it has the advantage of gene homology with human immune system. It may avoid harm of its residue in food to human immune system after spray of its preparation or transgenic expression.

In 1974, Danish immunologist Jerne introduced the concept of Anti-idiotype antibody in his "Immune Network Theory". Anti-idiotype antibody (hereafter referred to as Anti-Id) refers to the specific antibody generated to address the idiotype (hereinafter referred to as "Id") in the variable regions of antibody molecules. Bona, et al. classified Anti-Id into four types ($\alpha$, $\beta$, $\gamma$ and $\epsilon$) based on serological reaction between Id and Anti-Id as well as the function of AId. $\beta$-type Anti-Id has the effect of "internal image", i.e.: has antigenic determinant same as (haptin) antigen, so it may have the functions and bioactivity of antigen.

Currently, it is universally believed that Anti-Id with an effect similar to target antigen may be obtained by phage display technology through establishment of a phage antibody library, and specific screening. The process of screening specific antibody by phage display technology is called "Panning" and mainly includes four steps: binding, washing, eluting and amplification. Raats et al. adopted anti-cortisol monoclonal antibody coating as solid-phase antigen for direct screening. Before screening, a same species of negative monoclonal antibody is negatively screened to avoid screening recombinant antibody fragments bound to the constant region of antibody and successfully screen Anti-Id against cortisol. Goletz et al. also applied phage antibody display system and researched and compared the influence of different elution methods on Anti-Id fragment screening results. Of the eventually screened 96 clones, 28 were positive clones with Anti-Id characteristics. So far, no materials and products specific to substitutable Bt active effector, particularly Anti-Bt toxin type Anti-Id single-chain antibody (hereinafter referred to as "Anti-Id ScFvs") have been reported.

SUMMARY OF THE INVENTION

To address the potential safety hazard from the extensive application of transgenic Bt toxin crops and toxin preparations thereof, hypersensitivity and other problems at present, the present invention is realized through the development of a substitutable biological effector with Bt toxin bioactivity, and its application in biological control of pests:

A human-derived insect-resistant gene, having a nucleotide sequence represented by SEQ ID NO.1;

In the present invention, an anti-Cry1B toxin idiotype single-chain antibody encoded by SEQ ID NO.1, having an amino acid sequence represented by SEQ ID NO.2;

In the present invention, a prokaryotic expression vector containing human-derived insect-resistant gene SEQ ID NO.1;

In the present invention, an application of human-derived insect-resistant gene SEQ ID NO.1 in control of agricultural pests;

In the present invention, an insecticide containing anti-Cry1B toxin idiotype single-chain antibody with an amino acid sequence as represented by SEQ ID NO.2.

The present invention screened and obtained from disclosed human gene bank a "β"-type anti-Cry1B toxin idiotype single-chain antibody with insecticidal activity. After being expressed by the prokaryotic system, the primary culture of this single-chain antibody has binding activity to *Cnaphalocrocis medinalis* midgut peritrophic membrane specific receptor BBMV. The present invention obtains "β"-type anti-Cry1B toxin idiotype single-chain antibody without animal immunization. The preparation cycle is short. The amino acid sequence is small. It is suitable for in vitro mass production. Meanwhile, the present invention as a new insect-resistant gene resource has important scientific and practical significance to exploring and developing new-type insect-resistant gene resources simulating Bt toxin bioactivity to lower the safety risks from the wide use of existing Bt toxins and even substitute Bt in the future in biological control of agricultural pests and reduce the use of pesticides.

DETAILED DESCRIPTION OF THE EMBODIMENTS

Embodiment 1: Screen Human-Derived Insect-Resistant Gene

Figure 1:
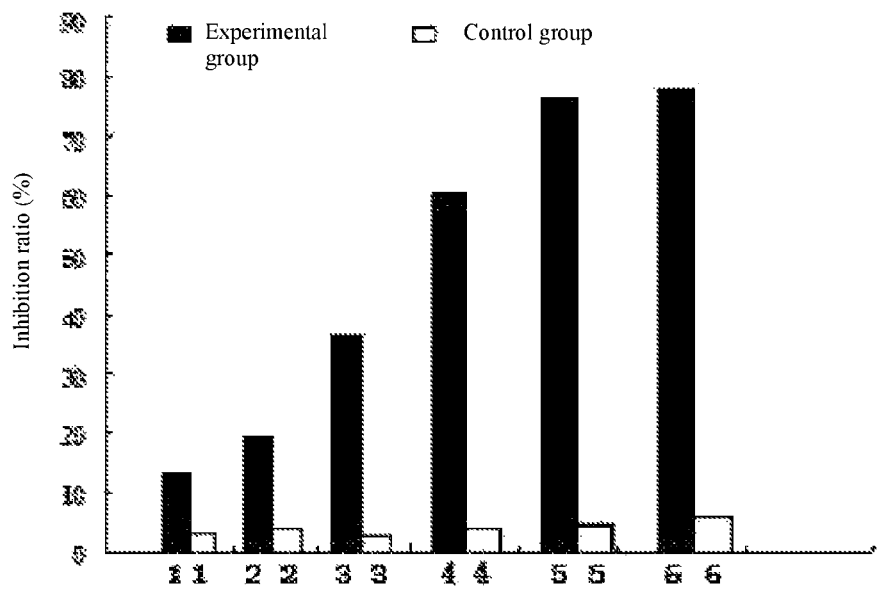
FIG. 1 is a schematic of C7 ELISA detection result.

Reagents and medium formulae involved in the embodiment:

(1) 2× TY Fluid Medium:
Add 16 g of tryptone, 10 g of yeast extract and 5 g of NaCl in 900 mL of double distilled water, mix them well, set the volume to 1 L by double distilled water, put the liquid in an autoclave, sterilize it at 121° C. for 20 minutes, cool it and store it at 4° C. for future use.

(2) 2×TY-AG Fluid Medium:
Add ampicillin with final concentration of 100 μg/ml and glucose with a mass ratio of 1% to 2×TY culture medium.

(3) 2×TY-AK Fluid Medium:
Add ampicillin with final concentration of 100 μg/ml and kanamycin with final concentration of 50 μg/ml to 2×TY culture medium.

(4) 2×TY-AKG Fluid Medium:
Add ampicillin with final concentration of 100 μg/ml, kanamycin with final concentration of 50 μg/ml and glucose with a mass ratio of 1% to 2×TY culture medium.

(5) TYE Solid Medium:
Add 15.0 g of agarose, 8 g of NaCl, 10 g of tryptone and 5 g of yeast extract to 900 ml of double distilled water, set the volume to 1 L by double distilled water, put the liquid in an autoclave, sterilize it at 121° C. for 20 minutes, cool it and store it at 4° C. for future use.

(6) TYE-AG Solid Medium:
Add ampicillin with final concentration of 100 μg/ml and glucose with a mass ratio of 1% to TYE Solid Medium.

(7) PBS Solution
Weigh 8.0 g of NaCl, 0.2 g of KCl, 2.9 g of $Na_2HPO_4 \cdot 12H_2O$ and 0.2 g of $KH_2PO_4$, add them in distilled water respectively, dissolve them thoroughly and set the volume to 1 L.

(8) PBST Solution
Add Tween-20 with a volume ratio of 0.05% to PBS solution.

(9) PEG/NaCl Solution:
Weigh 20 g of PEG 8000 and 14.61 g of NaCl, add 80 ml of deionized water, set the volume to 100 ml, put the solution in an autoclave, sterilize it at 121° C. for 20 minutes, cool it and store it at 4° C. for future use.

(10) Citrate Buffer Solution (CPBS, pH=5.5):
Weigh 21 g of $C_6H_7O_8$ (citric acid) and 71.6 g of $Na_2HPO_4 \cdot 12H_2O$, add them to distilled water respectively, dissolve them thoroughly and set the volume to 1 L.

(11) Tetramethyl Benaidine (TMB) Solution:
Weigh 10 mg of TMB, dissolve it in 1 ml of dimethyl sulfoxide, keep the solution in a dark place and store it at 4° C. for future use.

(12) Substrate Chromogenic Solution:
Composition of 10 ml formula: 9.875 ml of CPBS, 100 μl of TMB solution and 25 μl $H_2O_2$ at volume ratio of 20%.

Sources of the Materials in Involved the Embodiment:

Anti-Cry1B polyclonal antibody, BBMV, irrelevant Anti-Id single-chain antibody, non-"β"-type Anti-Id ScFv, cabbage leaves and *Plutella xylostella* third instar larvae were provided by the Key Laboratory for Agricultural Product Quality and Safety Control Technology and Standard of the Ministry of Agriculture, Jiangsu Academy of Agricultural Sciences;

Humanized phage antibody library, TG1 bacteria and helper phage KM13 were purchased from British Source BioScience;

HRP-goat-anti-M13-IgG was purchased from Wuhan Boster Biological Technology Co., Ltd.;

Cry1B toxin and Cry1Ab toxin were purchased from Shanghai Youlong Biotech Co., Ltd.;

Paddy leaves and *Cnaphalocrocis medinalis* third instar larvae were provided by Yangzhou Luyuan Bio-Chemical Co., Ltd.

Embodiment 1: Screen Anti-Cry1B Toxin Idiotype Single-Chain Antibody (1) Add 20 μl of humanized phage antibody library bacterium liquid to 200 ml of 2×TY-AG fluid medium, cultivate it at constant temperature 37° C. till $OD_{600}$ is 0.4, measure 50 ml of the bacterium liquid, add $1×10^{12}$ pfu of helper phage KM13 for superinfection, incubate the liquid at 37° C. for 30 minutes, then centrifuge it at 3300 g for 10 minutes, discard the supernate, use 100 ml of 2×TY-AKG fluid medium to resuspend the precipitate and cultivate it at 30° C. overnight; centrifuge it at 3300 g for 30 minutes next day, collect the supernate, add 20 ml of PEG/NaCl solution, keep it in ice bath for 1 h, then centrifuge it at 3300 g for 30 minutes and resuspend the precipitate by 4 ml of PBS; centrifuge the resuspension solution at 11600 g for 10 minutes, and the supernate is amplified phage antibody library;

(2) Use the amplified phage antibody library obtained in step 1 for four rounds of Panning: in the first round of Panning, coat 4 ml of 100 μg/ml anti-Cry1B polyclonal antibody to the bottom of a cell culture flask, keep it at 4° C. overnight, wash the cell culture flask with 1 ml of PBS for 3 times next day, then add 1 ml of thoroughly mixed amplified phage antibody library and 4 ml of 3% MPBS solution, put the flask on a shaking table, slowly shake it at room temperature for 1 h, let it rest for 1 h, remove the liquid in the culture flask, wash the flask with 1 ml of PBST solution for 20 times and add 1 ml of 10 mg/ml trypsin to elute the specifically bound phage antibody. The eluent is phage antibody obtained in the first round of Panning. The concentrations of the coated anti-Cry1B polyclonal antibody panned in the second, third and fourth rounds are 50 μg/ml, 25 μg/ml and 10 μg/ml respectively. The used phage antibody is the phage antibody obtained from the previous round of panning. The panning method is same as adopted in the first round. 10 μl of the phage antibody panned in the fourth round is used to infect 1 ml of TG1 bacteria in a logarithmic phase. After it is incubated at 37° C. for 1 h, it is coated on TYE-AG solid medium and cultivated at 37° C. overnight; next day, single colonies are picked randomly, incubated on a 96-well plate containing 100 W/well of 2×TY-AG fluid medium and cultivated at 37° C. overnight; next day, 41 of bacterium liquid is sucked from the well plate, transferred to a new 96-well plate and incubated at 37° C. for 2 h. 25 μl of helper phage KM13 with titer of $10^{12}$ is added to every well, incubated at 30° C. for 2 h, centrifuged at 1800 g for 10 minutes, the precipitate is resuspended with 150 W of 2×TY-AK fluid medium and then cultivated at 30° C. overnight. Next day, it is centrifuged at 1800 g for 30 minutes. The supernate is collected;

(3) 4 μg/ml anti-Cry1B polyclonal antibody is measured and added to a 96-well plate, 100 μl/well, and stored at 4° C. overnight. Next day, 100 μl of the supernate obtained in step 2 is added to every well. 100 μl of 2×TY-AK fluid medium is added to the negative control. They are kept in 37° C. water bath for 2 h. After the plate is washed with 250 μl/well of PBST, 100 μl of 1:5000 diluted HRP-goat-anti-M13-IgG is added to each well and incubated at 37° C. for 2 h. 100 μl of substrate chromogenic solution is added to each well and takes reaction at room temperature for 10 to 20 minutes till blue appears. Lastly 50 μl of 2 mol/L $H_2SO_4$ is added to each well to quickly terminate the reaction. $OD_{450}$ is determined by ELIASA. If $OD_{450}$ of the solution/$OD_{450}$ of negative control is greater than 2.1, it will be considered positive. The supernate in step 2 corresponding to this solution is the screened supernate containing anti-Cry1B toxin Idiotype single-chain antibody.

The nucleotide sequence of the screened anti-Cry1B toxin idiotype single-chain antibody determined by Sanger sequencing method is SEQ ID NO.1, as shown below:

```
attgtctgcg gccccgtgat ggtgatgatg atgtgcggcc gcccgtttga tttccaccttt    60
ggtcccttgg ccgaacgtag aaggataagc agcagcctgt tgacagtagt aagttgcaaa   120
atcttcaggt tgcagactgc tgatggtgag agtgaaatct gtcccagatc cactgccact   180
gaaccttgat gggacccccac tttgcaaaga ggatgcacta tagatcagga gcttaggggc   240
tttccctggt ttctgctgat accaatttaa atagctgcta atgctctgac ttgcccggca   300
agtgatggtg actctgtctc ctacagatgc agacagggag gatggagact gggtcatctg   360
gatgtccgtc gacccgccac cgccgctgcc acctccgcct gaaccgcctc caccgctcga   420
gacggtgacc agggttccct ggccccagta gtcaaaataa gcaccagatt tcgcacagta   480
atatacggcc gtgtcctcgg ctctcaggct gttcatttgc agatacagcg tgttcttgga   540
attgtctctg gagatggtga accggccctt cacggagtct gcgtaacctg tagcaccacc   600
attattagca atagttgaga cccactccag cccttccct ggagcctggc ggacccagct   660
catggcatag ctgctaaagg tgaatccaga ggctgcacag gagagtctca gggacccccc   720
aggctgtacc aagcctcccc cagactccaa cagctgcacc tcggccatgg ccggctgggc   780
cgcgagtaat aacaatccag cggctgccgt aggcaatagg tatttcatta tgactgtctc   840
ctgaaataga attgt                                                    855
```

After nucleotide translation, the amino acid sequence of screened anti-Cry1B toxin idiotype single-chain antibody determined by Sanger sequencing method is SEQ ID NO.2, as shown below:

```
                                                        H-CDR1
MKYLLPTAAAGLLLLAAQPAMAEVQLLESGGGLVQPGGSLRLSCAASGFTFSSYAMSWVR    60

H-CDR2
QAPGKGLEWVSTIANNGGATGYADSVKGRFTISRDNSKNTLYLQMNSLRAEDTAVYYCAK   120

H-CDR1                  -----Link-----
SGAYFDYWGQGTLVTVSSGGGGSGGGGSGGGGSTDIQMTQSPSSLSASVGDRVTITCRAS   180        L-CDR1

L-CDR2
QSISSYLNWYQQKPGKAPKLLIYSASSLQSGVPSRFSGSGSGTDFTLTISSLQPEDFATY   240

L-CDR3                        His-tag
YCQQAAAYPSTFGQGTKVEIKRAAAHHHHHHGAAEQKLISEEDLNGAASTP           291
```

The applicant names this anti-Cry1B toxin idiotype single-chain antibody as C7.

Embodiment 2: Prepare Primary Culture of C7

The supernate obtained through screening in Embodiment 1 and containing anti-Cry1B toxin idiotype single-chain antibody is transferred to 10 ml of 2×TY-AG fluid medium at a volume ratio of 1:100 and incubated at 37° C. for 2 h. 100 μl of helper phage KM13 with titer of $10^{12}$ is added for rescue, incubated at 30° C. for 2 h and centrifuged at 1800 g for 10 minutes. The supernate is removed. 2×TY-AK fluid medium is used to resuspend the precipitated bacteria. It is cultivated while being shaken at 30° C. 250 rpm overnight. Next day it is centrifuged at 1800 g for 30 minutes. Its supernate is supernate containing C7 primary culture.

Embodiment 3: Subtype Identification of C7

(1) ELISA Detection Experiment of Competitive Inhibition

The experiment adopts 6 experimental groups and corresponding control groups. Solutions are prepared based on Table 1.

TABLE 1

Preparation of solutions for ELISA detection experiment

| Group | C7 | Irrelevant Anti-Id single-chain antibody | 2 × TY fluid medium |
|---|---|---|---|
| Experimental group 1 | 5 μl |  | 45 μl |
| Control group 1 |  | 5 μl | 45 μl |
| Experimental group 2 | 10 μl |  | 40 μl |
| Control group 2 |  | 10 μl | 40 μl |
| Experimental group 3 | 20 μl |  | 30 μl |
| Control group 3 |  | 20 μl | 30 μl |
| Experimental group 4 | 30 μl |  | 20 μl |
| Control group 4 |  | 30 μl | 20 μl |
| Experimental group 5 | 40 μl |  | 10 μl |
| Control group 5 |  | 40 μl | 10 μl |
| Experimental group 6 | 50 μl |  |  |
| Control group 6 |  | 50 μl |  |

In Table 1, C7 is the supernate obtained in Embodiment 2 and containing C7 primary culture;

Add 50 μl of 10 μg/ml anti-Cry1B polyclonal antibody to the solutions prepared in Table 1 respectively, incubate them at 37° C. for 2 h, add them to a 96-well plate coated with 2 μg/ml Cry1B toxin respectively (the 96-well plate coated with 2 μg/ml Cry1B toxin is obtained by adding 2 μg/ml Cry1B toxin to a 96-well plate on the previous day, 100 μl/well and keeping it at 4° C. overnight), take reaction for 2 h; wash the plate with 250 μl/well of PBST for 3 times, add 100 μl/well of 1:5000 diluted HRP-goat anti-rabbit IgG incubate it at room temperature for 1 h; wash the plate with 250 μl/well of PBST for 3 times, add 100 μl/well of substrate chromogenic solution, take reaction at room temperature for 10 to 20 minutes till blue appears and in the end add 50 μl/well of 2 mol/L $H_2SO_4$ to quickly terminate the reaction; determine $OD_{450}$ by ELIASA.

The experimental results are as shown in FIG. 1. The inhibition ratio increases with the increase of C7 content. The control groups do not have the phenomenon of competitive inhibition, suggesting C7 is β-type Anti-Id single-chain antibody and can simulate Cry1B toxin to competitively bind with anti-Cry1B toxin polyclonal antibody.

(2) Biological Determination Experiment

The experiment has experimental group 1, experimental group 2, experimental group 3, positive control group, negative control group 1, negative control group 2 and negative control group 3; the experimental procedure is as follows:

(a) Blocking: Coat 100 μl/well of 5 μg/ml BBMV in a 96-well plate, keep it at 4° C. overnight, wash the plate with 250 μl/well of PBST for 3 times next day, add 200 μl of BAS with a mass ratio of 3% respectively, incubate it at room temperature for 2 h, and carry out blocking;

(b) Sample addition: Wash the 96-well plate blocked in step 1 with 250 μl/well of PBST for 3 times, and add samples to the 96-well plate according to Table 2:

TABLE 2

Preparation of solutions for biological determination experiment of C7

| Group | 2 μg/ml Cry1B toxin | C7 | Non-"β"-type Anti-Id ScFv | 2 × TY-AG fluid medium | CPBS |
|---|---|---|---|---|---|
| Experimental group 1 | 50 μl | 10 μl |  | 40 μl |  |
| Experimental group 2 | 50 μl | 30 μl |  | 20 μl |  |
| Experimental group 3 | 50 μl | 50 μl |  |  |  |
| Positive control group | 50 μl |  |  |  | 50 μl |
| Negative control group 1 | 50 μl |  | 10 μl | 40 μl |  |
| Negative control group 2 | 50 μl |  | 30 μl | 20 μl |  |
| Negative control group 3 | 50 μl |  | 50 μl |  |  |

In Table 2, C7 is the supernate obtained in Embodiment 2 and containing C7 primary culture;

(c) Incubate the 96-well plate added with sample in step b at room temperature for 2 h, wash the plate with 250 μl/well of PBST for 3 times, add 100 μl/well of 10 μg/ml anti-Cry1B polyclonal antibody, then wash the plate with 250 μl/well of PBST for 3 times, add 100 μl/well of 1:5000 diluted HRP-goat anti-rabbit IgG and incubate it at room temperature for 1 h; wash the plate with 250 μl/well of PBST for 3 times, add 100 μl/well of substrate chromogenic solution per well, take reaction at room temperature for 10 to 20 minutes till blue appears and in the end add 50 μl/well of 2 mol/L $H_2SO_4$ to quickly terminate the reaction, and determine $OD_{450}$ by ELIASA.

Figure 2:
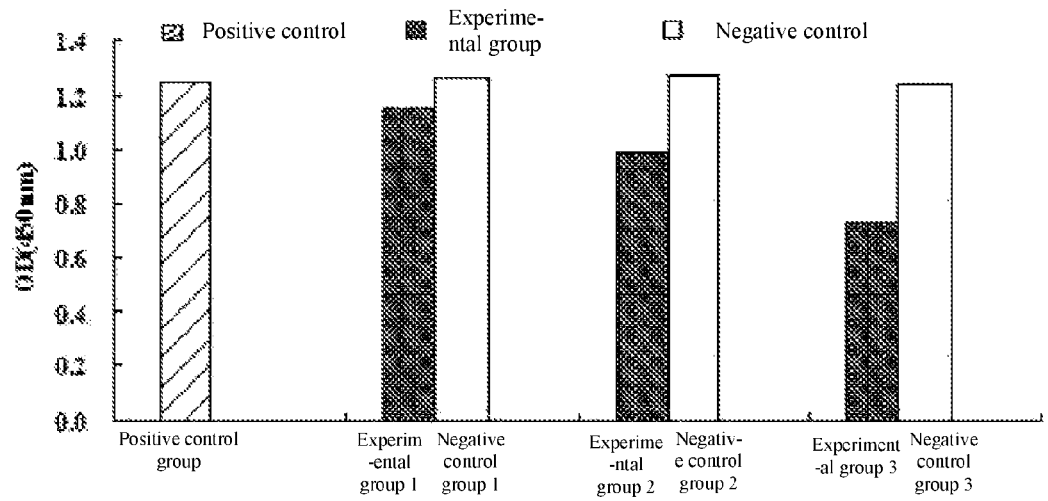
FIG. 2 is a schematic of C7 biological determination result.

The experimental result is as shown in FIG. 2. Compared with positive control, anti-Cry1B toxin idiotype single-chain antibody C7 (experimental groups 1, 2 and 3) can inhibit the binding between Cry1B toxin and its receptor BBMV; non-"β"-type negative control does not have the phenomenon of inhibition, which further proves that C7 is "β" type.

Embodiment 4: Verify Insecticidal Activity of Anti-Cry1B Toxin Idiotype Single-Chain Antibody The experiment has experimental groups and control groups:
The experimental groups use the supernate (C7) obtained in Embodiment 2 and containing C7 primary culture;
The positive control groups adopt 0.2 g/L Cry1Ab toxin (CK+);
The negative control groups adopt non-"β" type Anti-Id ScFvs (CK−);
Experimental Procedure:
Measure experimental groups, positive control groups and negative control groups each 10 ml, put them in sterilized culture dishes, add 6 paddy leaves and 6 cabbage leaves respectively, soak them for 30 minutes, take them out and dry them in the air; feed Cnaphalocrocis medinalis third instar larvae and Plutella xylostella third instar larvae with dried leaves.

Figure 3:
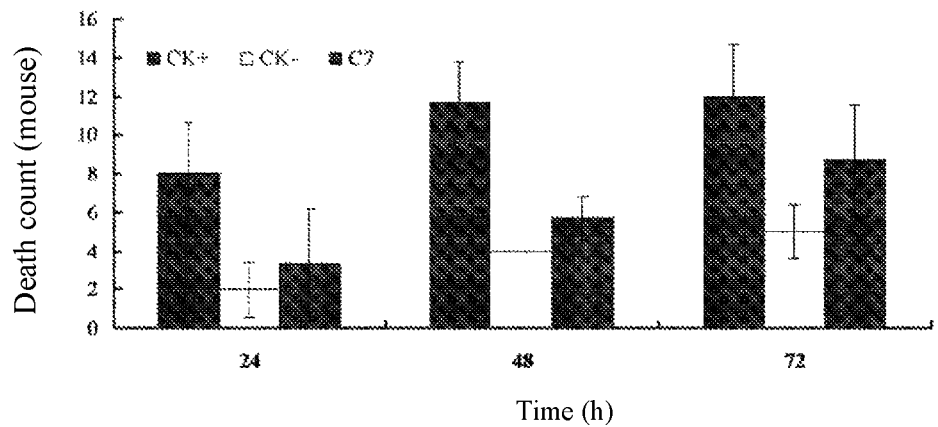
FIG. 3 is a schematic showing the death condition of *Cnaphalocrocis medinalis* third instar larvae after they were fed with paddy leaves soaked with C7, CK+ and CK− respectively.
Figure 4:
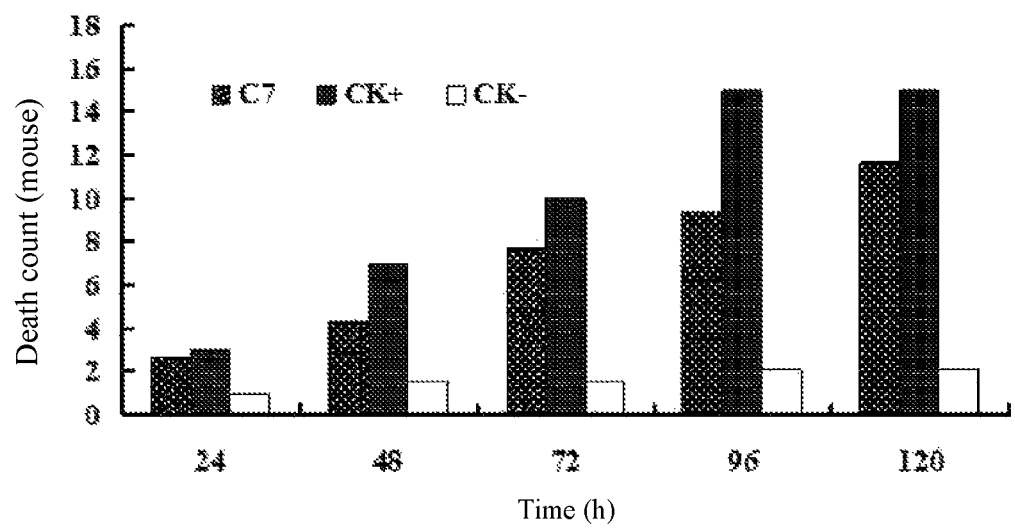
FIG. 4 is a schematic showing the death condition of *Plutella xylostella* third instar larvae after they were fed with cabbage leaves soaked with C7, CK+ and CK− respectively.

The experimental result is as shown in FIG. 3 and FIG. 4. FIG. 3 shows the death condition of Cnaphalocrocis medinalis third instar larvae respectively fed with paddy leaves, which have been soaked with C7, Cry1Ab toxin (CK+) and non-"β"-type Anti-Id ScFvs (CK−). FIG. 4 shows the death condition of Plutella xylostella third instar larvae respectively fed with cabbage leaves, which have been soaked with C7, Cry1Ab toxin (CK+) and non-"β"-type Anti-Id ScFvs (CK−). It can be seen that C7 has a good insecticidal effect.

What is claimed is:

1. A single-chain antibody comprising the amino acid sequence of SEQ ID NO.2.

2. An insecticide comprising a single-chain antibody, wherein the single-chain antibody comprises the amino add sequence of represented by SEQ ID NO.2.

* * * * *

SEQUENCE LISTING

<160> NUMBER OF SEQ ID NOS: 2

<210> SEQ ID NO 1
<211> LENGTH: 855
<212> TYPE: DNA
<213> ORGANISM: Artificial Sequence
<220> FEATURE:
<223> OTHER INFORMATION: Artificially synthesized

<400> SEQUENCE: 1

```
attgtctgcg gccccgtgat ggtgatgatg atgtgcggcc gcccgtttga tttccacctt      60
ggtcccttgg ccgaacgtag aaggataagc agcagcctgt tgacagtagt aagttgcaaa     120
atcttcaggt tgcagactgc tgatggtgag agtgaaatct gtcccagatc cactgccact     180
gaaccttgat gggaccccac tttgcaaaga ggatgcacta tagatcagga gcttaggggc     240
tttccctggt ttctgctgat accaatttaa atagctgcta atgctctgac ttgcccggca     300
agtgatggtg actctgtctc ctacagatgc agacagggag gatggagact gggtcatctg     360
gatgtccgtc gacccgccac cgccgctgcc acctccgcct gaaccgcctc caccgctcga     420
gacggtgacc agggttccct ggccccagta gtcaaaataa gcaccagatt tcgcacagta     480
atatacggcc gtgtcctcgg ctctcaggct gttcatttgc agatacagcg tgttcttgga     540
attgtctctg gagatggtga accggccctt cacggagtct gcgtaacctg tagcaccacc     600
attattagca atagttgaga cccactccag ccccttccct ggagcctggc ggacccagct     660
catggcatag ctgctaaagg tgaatccaga ggctgcacag gagagtctca gggacccccc     720
aggctgtacc aagcctcccc cagactccaa cagctgcacc tcggccatgg ccggctgggc     780
cgcgagtaat aacaatccag cggctgccgt aggcaatagg tatttcatta tgactgtctc     840
ctgaaataga attgt                                                       855
```

<210> SEQ ID NO 2
<211> LENGTH: 291
<212> TYPE: PRT
<213> ORGANISM: Artificial Sequence
<220> FEATURE:
<223> OTHER INFORMATION: Artificially synthesized

<400> SEQUENCE: 2

-continued

```
Met Lys Tyr Leu Leu Pro Thr Ala Ala Ala Gly Leu Leu Leu Ala
1               5                   10                  15

Ala Gln Pro Ala Met Ala Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ser Thr Ile Ala Asn Asn Gly Gly Ala Thr
65                  70                  75                  80

Gly Tyr Ala Asp Ser Val Lys Gly Arg Phe Thr Ile Ser Arg Asp Asn
            85                  90                  95

Ser Lys Asn Thr Leu Tyr Leu Gln Met Asn Ser Leu Arg Ala Glu Asp
                100                 105                 110

Thr Ala Val Tyr Tyr Cys Ala Lys Ser Gly Ala Tyr Phe Asp Tyr Trp
            115                 120                 125

Gly Gln Gly Thr Leu Val Thr Val Ser Ser Gly Gly Gly Ser Gly
        130                 135                 140

Gly Gly Gly Ser Gly Gly Gly Ser Thr Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Ser Ala Ser Ser Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Ala Ala Ala Tyr Pro Ser Thr Phe Gly Gln Gly Thr
            245                 250                 255

Lys Val Glu Ile Lys Arg Ala Ala Ala His His His His His His Gly
            260                 265                 270

Ala Ala Glu Gln Lys Leu Ile Ser Glu Glu Asp Leu Asn Gly Ala Ala
            275                 280                 285

Ser Thr Pro
    290
```